(12) United States Patent
Hibner

(10) Patent No.: US 8,277,394 B2
(45) Date of Patent: Oct. 2, 2012

(54) MULTI-BUTTON BIOPSY DEVICE

(75) Inventor: John A. Hibner, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 482 days.

(21) Appl. No.: 12/542,775

(22) Filed: Aug. 18, 2009

(65) Prior Publication Data

US 2011/0046513 A1 Feb. 24, 2011

(51) Int. Cl.
*A61B 10/00* (2006.01)
(52) U.S. Cl. ......... 600/568; 600/562; 600/564; 600/567
(58) Field of Classification Search .................. 600/562, 600/564–568, 572, 583
See application file for complete search history.

(56) References Cited

U.S. PATENT DOCUMENTS

| | | | |
|---|---|---|---|
| 5,469,853 | A | 11/1995 | Law et al. |
| 5,526,822 | A | 6/1996 | Burbank et al. |
| 6,086,544 | A | 7/2000 | Hibner et al. |
| 6,626,849 | B2 | 9/2003 | Huitema et al. |
| 7,229,419 | B2 | 6/2007 | Hancock |
| 7,442,171 | B2 | 10/2008 | Stephens et al. |
| 7,452,356 | B2 | 11/2008 | Grove et al. |
| 2006/0074345 | A1 | 4/2006 | Hibner |
| 2008/0214955 | A1 | 9/2008 | Speeg et al. |
| 2009/0171242 | A1 | 7/2009 | Hibner |

FOREIGN PATENT DOCUMENTS

EP 2 074 949 7/2009

OTHER PUBLICATIONS

International Search Report dated Sep. 2, 2010 for Application No. PCT/US2010/040315.
Written Opinion dated Sep. 2, 2010 for Application No. PCT/US2010/040315.
U.S. Appl. No. 12/335,578, filed Dec. 16, 2008, Parihar et al.
U.S. Appl. No. 12/337,874, filed Dec. 18, 2008, Parihar et al.
U.S. Appl. No. 12/337,911, filed Dec. 18, 2008, Parihar et al.
U.S. Appl. No. 12/337,942, filed Dec. 18, 2008, Parihar et al.
U.S. Appl. No. 12/337,997, filed Dec. 18, 2008, Parihar.
U.S. Appl. No. 12/483,305, filed Jun. 12, 2009, Hibner et al.

*Primary Examiner* — Jeffrey G Hoekstra
(74) *Attorney, Agent, or Firm* — Frost Brown Todd LLC

(57) ABSTRACT

A handheld biopsy device comprises a needle, cutter, and body. The cutter is movable relative to the needle to sever tissue protruding into a transverse aperture of the needle. The body includes a cutter actuation mechanism, at least two trigger buttons, and a control module. The biopsy device is configured such that the at least two trigger buttons are selectively enabled and disabled. A selectively enabled trigger button is operable to activate the cutter actuation mechanism. A selectively disabled trigger button is not operable to activate the cutter activation mechanism. The enabled trigger button may be selected electronically, such that the control module receives a user's button selection input and enables or disables the trigger buttons accordingly. Alternatively, the body may include movable covers to selectively cover or expose trigger buttons in accordance with the user's preference. The biopsy device may thus accommodate different operators having different gripping styles.

19 Claims, 8 Drawing Sheets

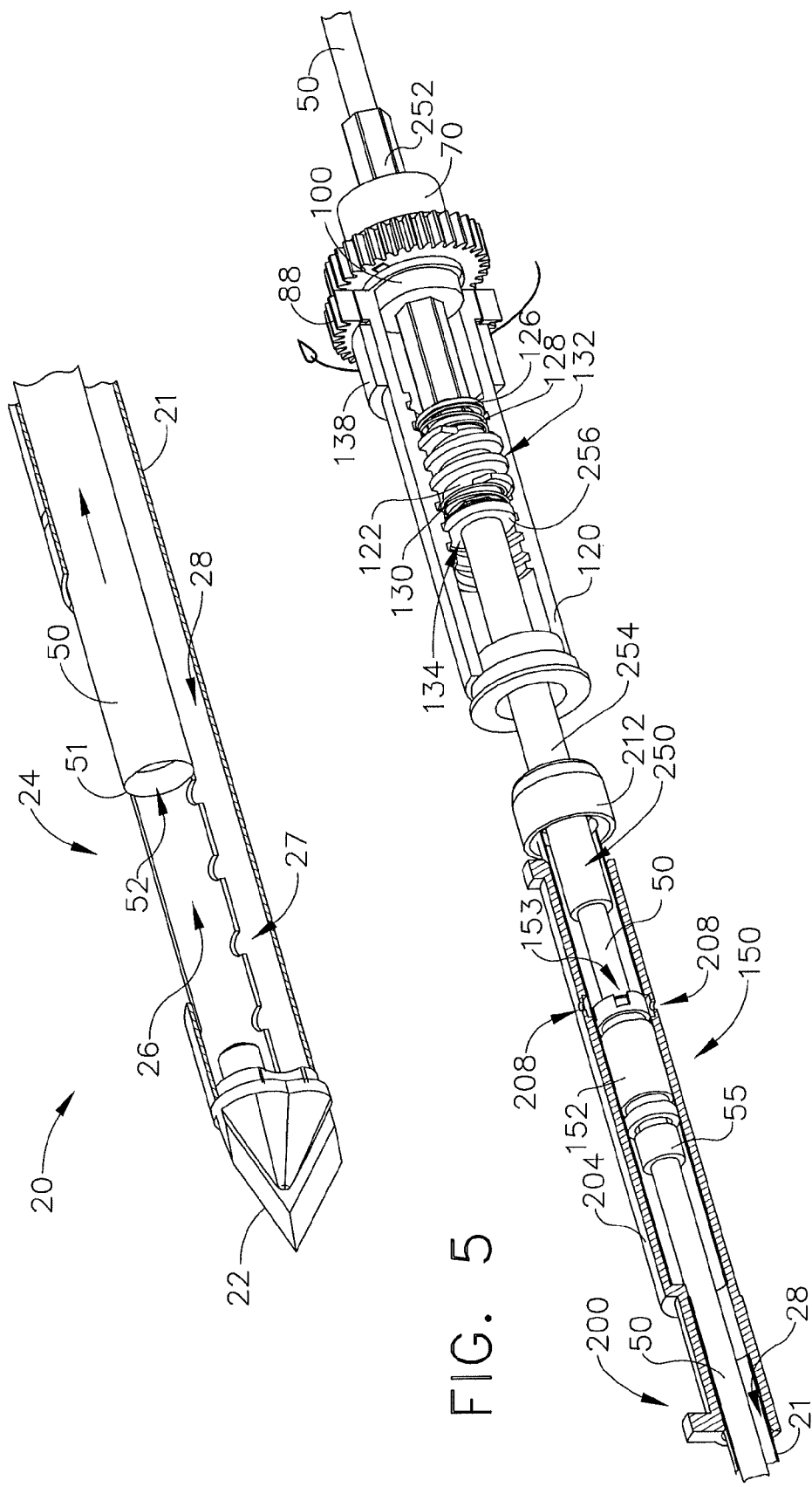

MULTI-BUTTON BIOPSY DEVICE

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Non-Provisional patent application Ser. No. 11/964,811, entitled "Clutch and Valving System for Tetherless Biopsy Device," filed Dec. 27, 2007; U.S. Non-Provisional patent application Ser. No. 12/335,578, entitled "Hand Actuated Tetherless Biopsy Device with Pistol Grip," filed Dec. 16, 2008; and U.S. Non-Provisional patent application Ser. No. 12/337,942, entitled "Biopsy Device with Central Thumbwheel," filed Dec. 18, 2008. The disclosure of each of the above-cited U.S. Patents, U.S. Patent Application Publications, and U.S. Non-Provisional Patent Application is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 5 depicts a perspective cross-sectional view of a needle portion of the biopsy device of FIG. 1, with the cutter in a partially retracted position;

FIG. 6 depicts a perspective cross-sectional view of cutter actuation mechanism and valve mechanism components of the biopsy device of FIG. 1, with the cutter in the partially retracted position of FIG. 5;

Figure 1:
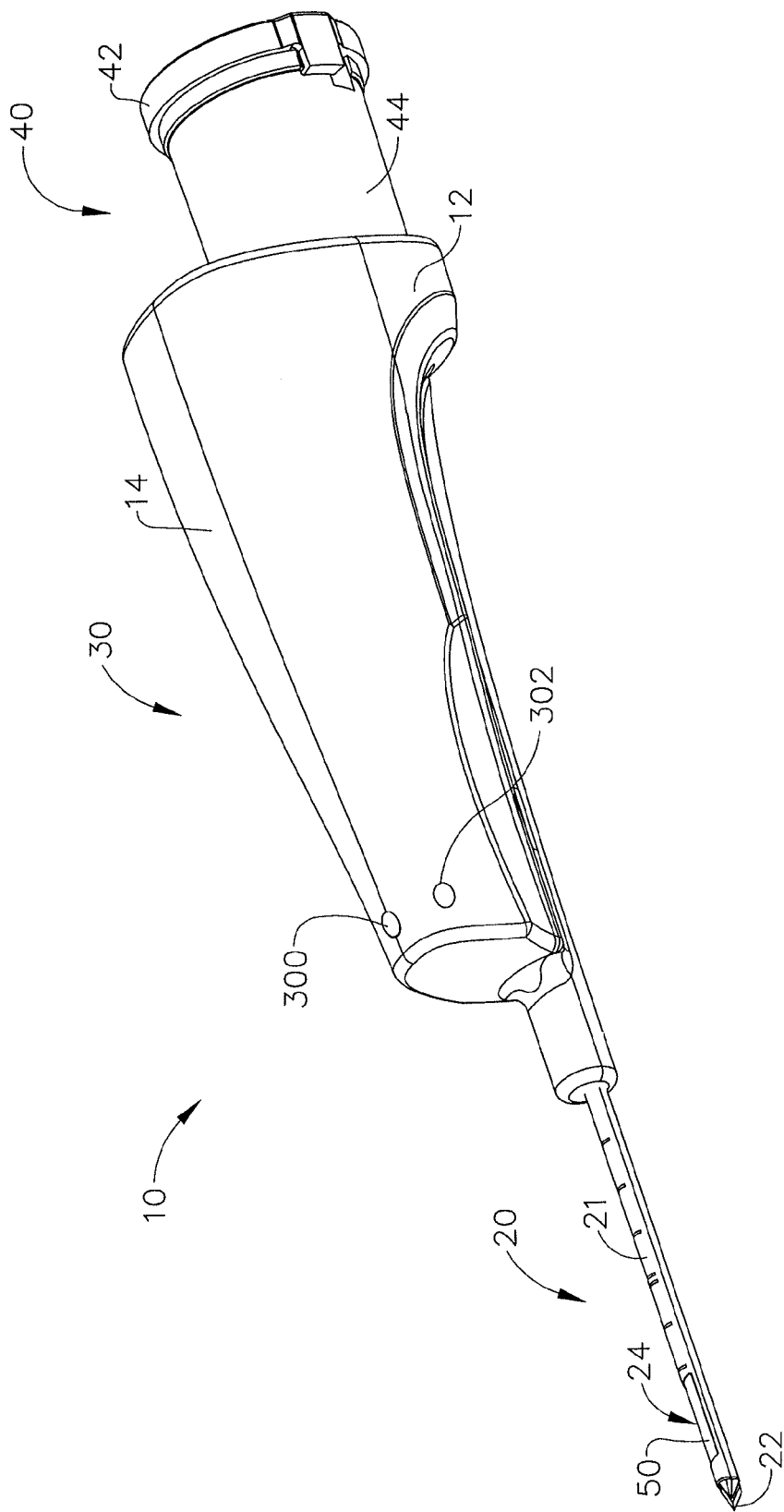
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Overview

Figure 2:
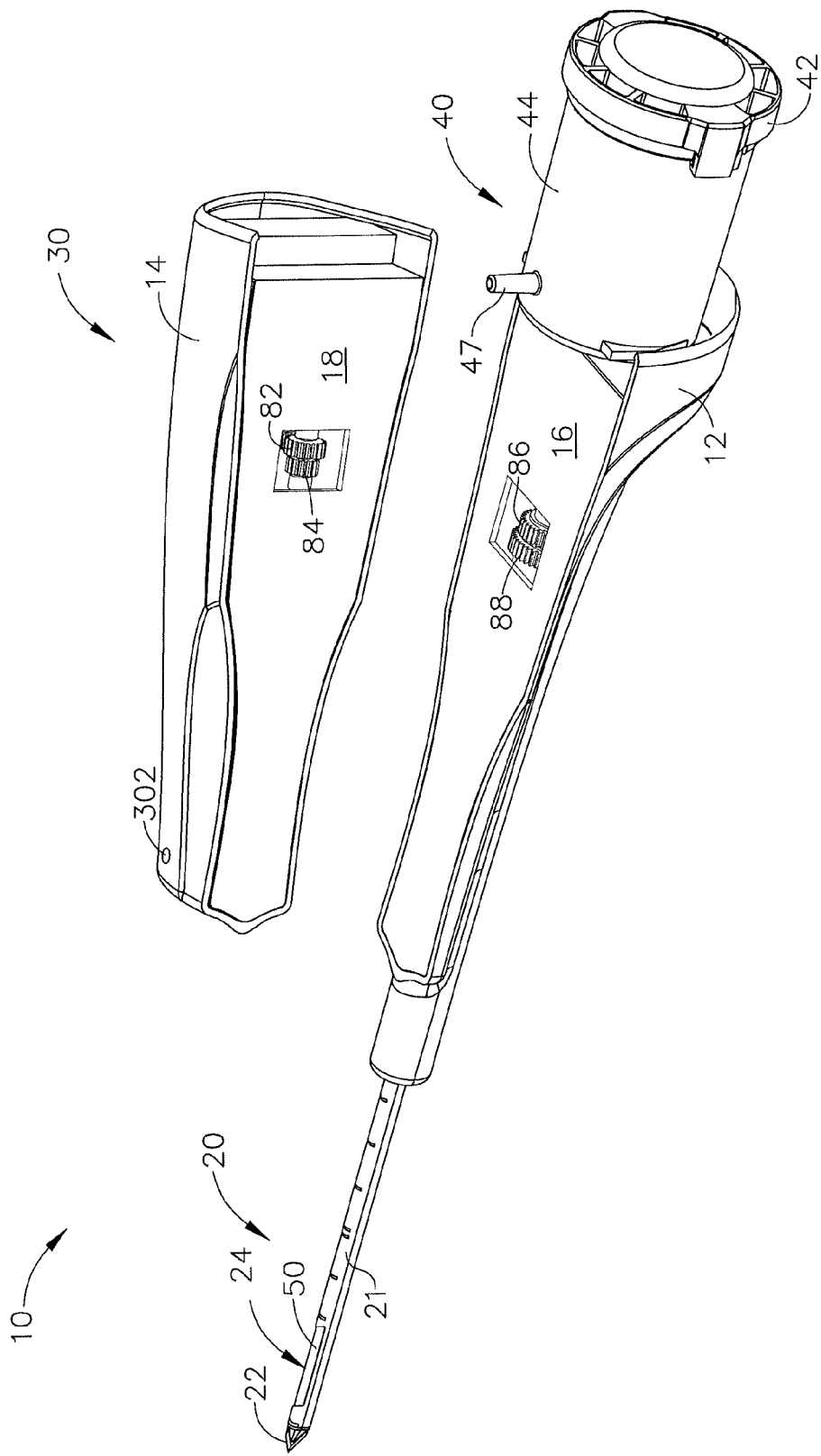
FIG. 2 depicts a perspective view of the biopsy device of FIG. 1, with a probe portion separated from a holster portion.
Figure 3:
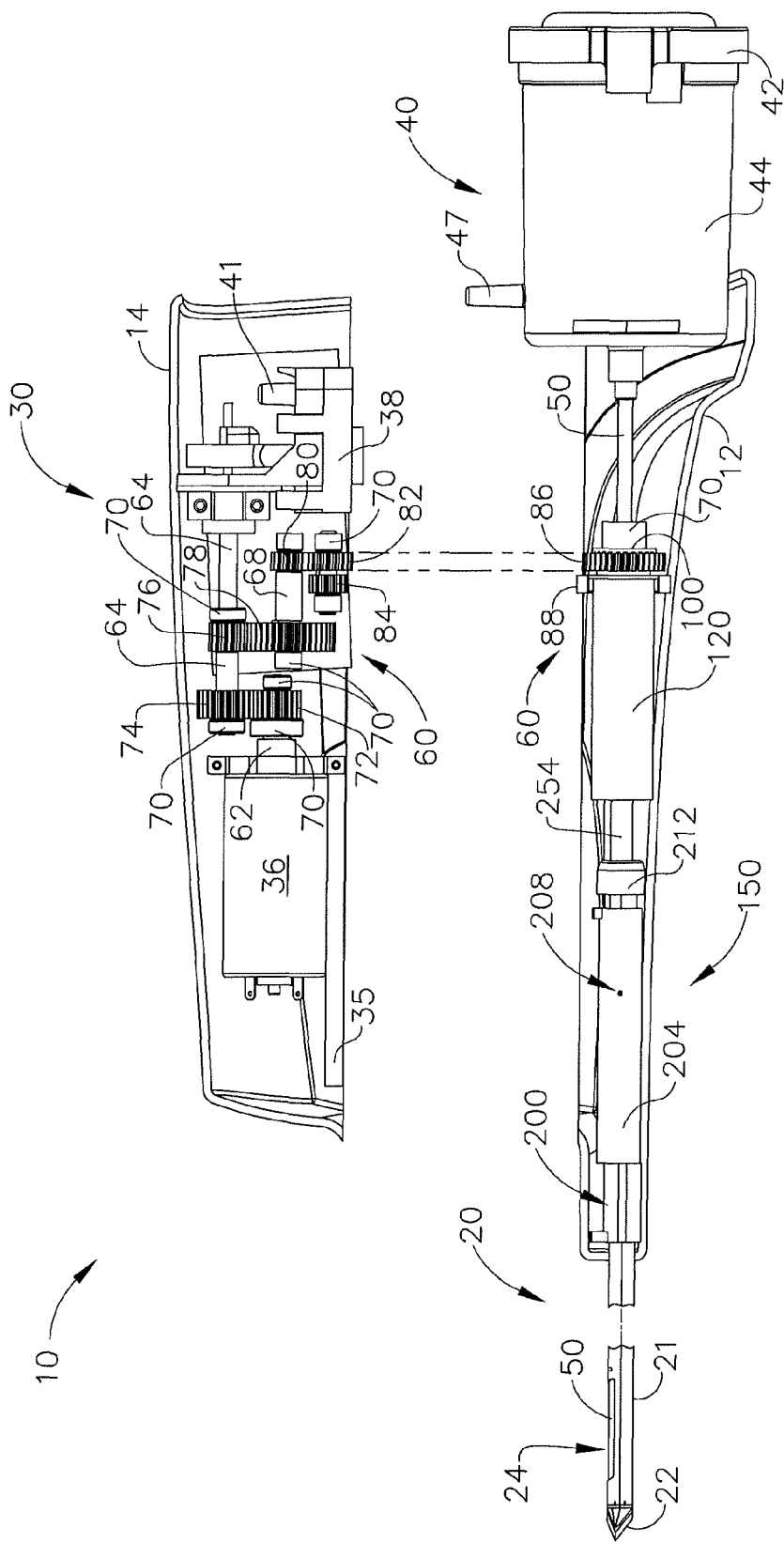
FIG. 3 depicts a side cross-sectional view of the biopsy device of FIG. 1, with the probe portion separated from the holster portion.

As shown in FIGS. 1-3 (among others), an exemplary biopsy device (10) comprises a needle (20), a body (30), and a tissue sample holder (40). In particular, needle (20) extends distally from the distal portion of body (30), while tissue sample holder (40) extends proximally from the proximal portion of body (30). Body (30) is sized and configured such that biopsy device (10) may be operated by a single hand of a user. In particular, and as described in greater detail below, a user may grasp body (30) with a single hand, insert needle (20) into a patient's breast, and collect one or a plurality of tissue samples from within the patient's breast, all with just using a single hand. Alternatively, a user may grasp body (30) with more than one hand and/or with any desired assistance. In some settings, the user may capture a plurality of tissue samples with just a single insertion of needle (20) in the patient's breast. Such tissue samples may be pneumatically deposited in tissue sample holder (40), as described in greater detail below, then retrieved from tissue sample holder (40) for analysis.

Body (30) of the present example comprises a probe (12) and a holster (14). As shown in FIGS. 2-3, and as described in greater detail below, probe (12) is separable from holster (14). In particular, probe (12) and holster (14) may be removably coupled using bayonet mounts (not shown) or any other suitable structures or features. Use of the term "holster" herein should not be read as requiring any portion of probe (12) to be inserted into any portion of holster (14). Indeed, in some variations of biopsy device (10), probe (12) may simply sit on holster (14). In some other variations, a portion of holster (14) may be inserted into probe (12). Furthermore, in some biopsy devices (10), probe (12) and holster (14) may be of unitary or integral construction, such that the two components cannot be separated. By way of example only, in versions where probe (12) and holster (14) are provided as separable components, probe (12) may be provided as a disposable component, while holster (14) may be provided as a reusable component. In some versions, holster (14) is "activated" or powered up when probe (12) is coupled therewith. In some other versions, holster (14) is "activated" or powered up when holster (14) is removed from a charging base (not shown). Still other suitable structural and functional relationships between probe (12) and holster (14), as well as various ways in which holster (14) may be activated, will be apparent to those of ordinary skill in the art in view of the teachings herein.

While examples described herein refer to the acquisition of biopsy samples from a patient's breast, it should be understood that biopsy device (10) may be used in a variety of other procedures for a variety of other purposes and in a variety of other parts of a patient's anatomy.

Exemplary Needle

Figure 7:
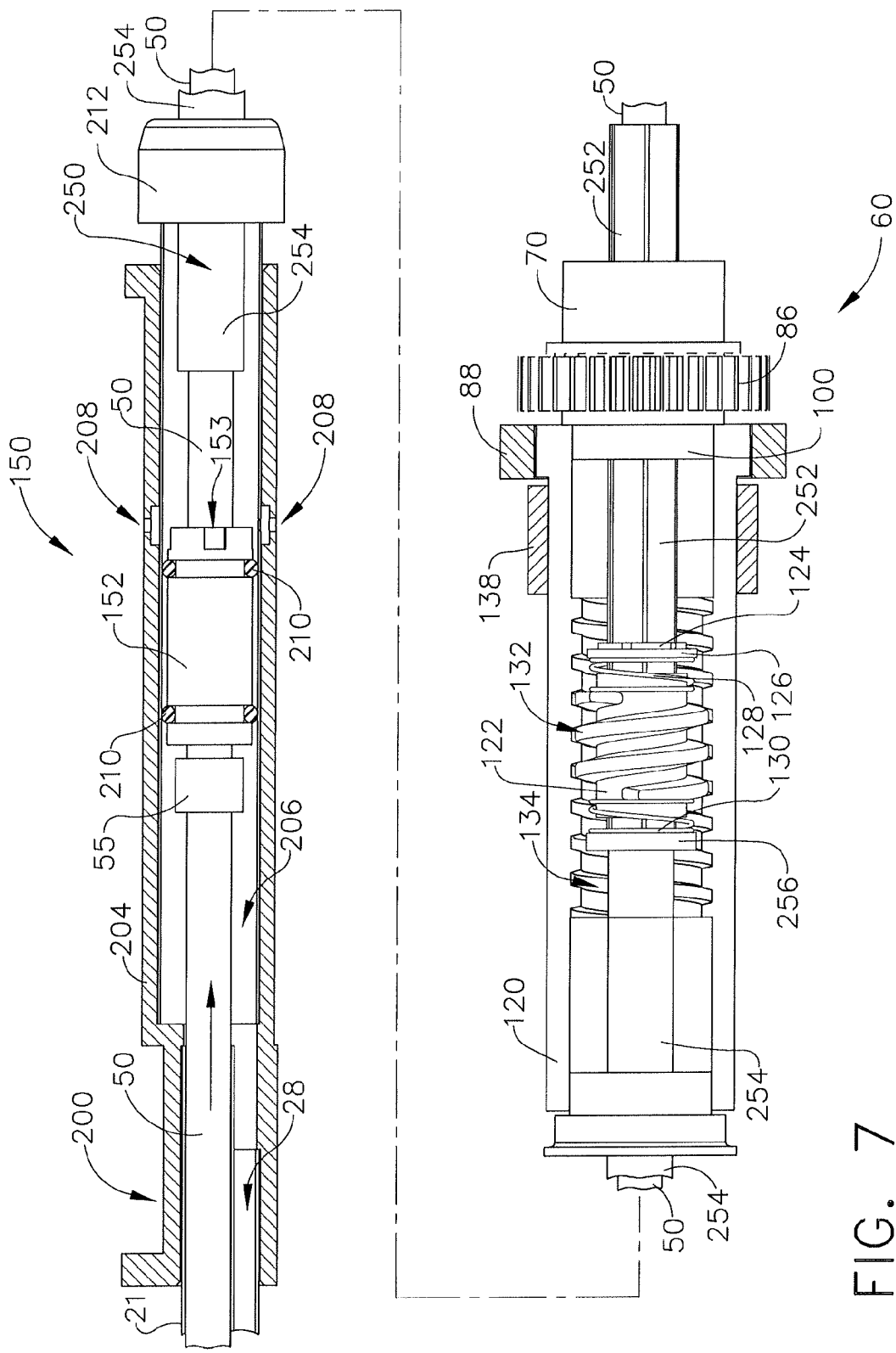
FIG. 7 depicts a side cross-sectional view of the components of FIG. 6, with the cutter in the partially retracted position of FIG. 5.

As shown in FIG. 5 (among others), needle (20) of the present example comprises a cannula (21) with a tissue piercing tip (22), a lateral aperture (24), a first lumen (26), and a second lumen (28). Tissue piercing tip (22) is configured to pierce and penetrate tissue, without requiring a high amount of force, and without requiring an opening to be pre-formed in the tissue prior to insertion of tip (22). A cutter (50) is disposed in first lumen (26), and is operable to rotate and translate within first lumen (26) as will be described in greater detail below. Lateral aperture (24) is located proximal to tip (22), is in fluid communication with first lumen (26), and is configured to receive tissue when needle (20) is inserted in a breast and when a cutter (50) is retracted as will also be described in greater detail below. A plurality of openings (27) provide fluid communication between first and second lumens (26, 28). Needle (20) of the present example further comprises a hub (200), as shown in FIGS. 6-7. Hub (200) may be formed of plastic that is overmolded about needle (20) or otherwise secured to needle (20), such that hub (200) is unitarily secured to needle (20). Alternatively, hub (200) may be formed of any other suitable material through any suitable process and may have any other suitable relationship with needle (20).

Hub (200) of the present example comprises a sleeve portion (204), which extends integrally into probe portion (12) of body (30). As shown in FIGS. 6-7, sleeve portion (204) defines a hollow interior (206), which is in fluid communication with second lumen (28) of needle (20). Sleeve portion (204) also defines a plurality of openings (208), which are radially spaced about the perimeter of sleeve portion (204) at a common longitudinal position, and which are in fluid communication with hollow interior (206). Openings (208) are exposed to ambient air, such that openings (208) provide a vent in the present example. Openings (208) are selectively fluidly coupled with second lumen (28) of needle (20) in this example, as will be described in greater detail below. A pair of o-rings (210) are positioned about a shuttle valve slider (152), to substantially seal second lumen (28) relative to openings (208) when second lumen (28) is not to be vented, depending on the longitudinal position of slider (152) as will be described in greater detail below. A seal (212) is also provided at the proximal end of sleeve (204), at the interface of cutter (50) and sleeve (204).

It should be understood that, as with other components described herein, needle (20) may be varied, modified, substituted, or supplemented in a variety of ways; and that needle (20) may have a variety of alternative features, components, configurations, and functionalities. By way of example only, needle (20) may simply lack second lumen (28) altogether in some versions, such that first lumen (26) is the only lumen defined by needle (20). As another merely exemplary alternative, biopsy device (10) may be configured such that needle (20) may be fired distally relative to body (30), such as to assist in penetration of tissue. Such firing may be provided by one or more actuators (e.g., solenoid, pneumatic cylinder/piston, etc.), by one or more springs, or in any other suitable fashion. Other suitable alternative versions, features, components, configurations, and functionalities of needle (20) will be apparent to those of ordinary skill in the art in view of the teachings herein. Similarly, other suitable modifications to other components of biopsy device (10) that may be made in accordance with variations of needle (20) (e.g., modifying or omitting valve mechanism (150) in versions where second lumen (28) is omitted from needle (20), etc.) will be apparent to those of ordinary skill in the art in view of the teachings herein.

Exemplary Body

Figure 4:
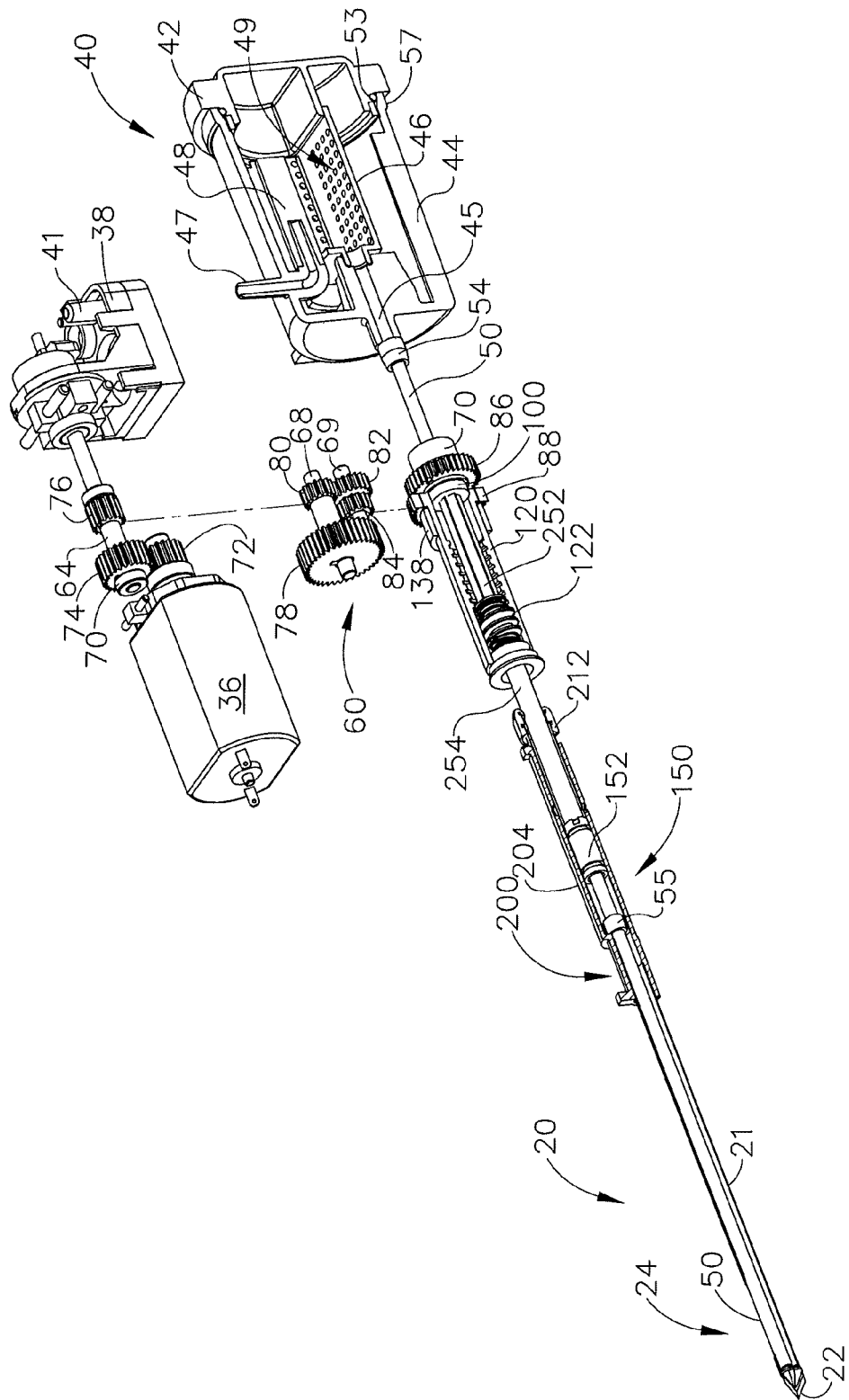
FIG. 4 depicts an exploded view of the biopsy device of FIG. 1, with portions shown in cross-section, and with housing components, a battery, and a circuit board removed.

As noted above, body (30) of the present example comprises a probe portion (12) and a holster portion (14). As shown in FIGS. 3-4, a motor (36), a vacuum pump (38), a battery (320), and a control module (330) are provided within holster portion (14). Battery (320) may be coupled with motor (36) via control module (330) and one or more trigger buttons (300, 302, 304), as will be described in greater detail below.

As shown in FIGS. 3-4, motor (36) of the present example is in mechanical communication with vacuum pump (38) and a cutter actuation mechanism (60). In particular, motor (36) is operable to simultaneously activate vacuum pump (38) and cutter actuation mechanism (60) when motor (36) is activated. Alternatively, vacuum pump (38) and cutter rotation mechanism (60) may be activated in any other suitable fashion. By way of example only, vacuum pump (38) and/or cutter rotation mechanism (60) may be activated manually and/or by separate motors and/or in any other suitable fashion. Motor (36) of the present example comprises a conventional DC motor. However, it should be understood that motor (36) may alternatively comprise a pneumatic motor (e.g., with impeller, etc.), a pneumatic linear actuator, an electromechanical linear actuator, or a variety of other types of movement-inducing devices. Various suitable ways in which other types of movement-inducing devices may be incorporated into biopsy device (10) will be apparent to those of ordinary skill in the art in view of the teachings herein.

As shown in FIGS. 3-4, a drive shaft (62) extends from motor (36), and is rotationally driven by motor (36). A pair of bearings (70) and a drive gear (72) are positioned about drive shaft (62). Bearings (70) support drive shaft (62), while drive gear (72) rotates unitarily with drive shaft (62). Drive gear (72) meshes with a second gear (74), which is unitarily secured to a second shaft (64). Second shaft (64) also includes associated bearings (70) and a third gear (76).

Vacuum pump (38) of the present example comprises a conventional diaphragm pump, which is driven by a second shaft (64), which is in turn rotationally driven by motor (36) as described above. Vacuum pump (38) of the present example operates in the same way regardless of which direction motor (36) rotates. Of course, any other suitable type of vacuum pump may be used. Vacuum pump (38) of the present example is operable to induce a vacuum in tissue sample holder (40) when vacuum pump (38) is activated, as will be described in greater detail below.

It should be understood that, as with other components described herein, body (30) may be varied, modified, substituted, or supplemented in a variety of ways; and that body (30) may have a variety of alternative features, components, configurations, and functionalities. Suitable alternative versions, features, components, configurations, and functionalities of body (30) will be apparent to those of ordinary skill in the art in view of the teachings herein.

Exemplary Valve Mechanism

As shown in FIGS. 4 and 6-7, biopsy device (10) also includes a valve mechanism (150) in the present example. Valve mechanism (150) of this example comprises shuttle valve slider (152), o-rings (210), and sleeve (204) of needle hub (200). Shuttle valve slider (152) is positioned coaxially about cutter (50), longitudinally between the distal end of sleeve (250) and the proximal end of a stop member (55), and is configured to translate relative to sleeve (204) and relative to cutter (50). O-rings (210) are configured to seal the exterior of shuttle valve slider (152) against the interior sidewall of sleeve (204). A gap provides longitudinal fluid communication (e.g., atmospheric air, etc.) between the outer diameter of cutter (50) and the inner diameter of shuttle valve slider (152). Notches (153) are configured to provide fluid communication to the interior of shuttle valve slider (152), even as the distal end of smooth portion (254) of sleeve (250) engages the proximal end of shuttle valve slider (152).

As described in greater detail below, cutter (50) is configured to rotate and translate relative to body (30), while sleeve (204) remains substantially stationary relative to body (30). Sleeve (250) and stop member (55) translate unitarily with cutter (50). In addition, stop member (55) may push shuttle valve slider (152) proximally; while sleeve (250) may push shuttle valve slider (152) distally. Shuttle valve slider (152) may thus translate within sleeve (250) in accordance with translation of cutter (50) relative to body (30). However, the distance between the distal end of sleeve (250) and the proximal end of stop member (55) is greater than the length of shuttle valve slider (152), such that there is a degree of "lost motion" between shuttle valve slider (152) and cutter (50) as cutter (50) translates in the present example. An example of such action of shuttle valve slider (152) is disclosed in U.S. Non-Provisional patent application Ser. No. 12/483,305, entitled "Tetherless Biopsy Device with Reusable Portion," filed Jun. 12, 2009, the disclosure of which is incorporated by reference herein.

In the present example, shuttle valve slider (152) remains distal to openings (208), thereby venting second lumen (28), when cutter (50) is at a distal-most position; when cutter (50) is transitioning between the distal-most position and the proximal-most position (see, e.g., FIGS. 5-7); and at latter stages of cutter (50) transitioning from the proximal-most position to the distal-most position. However, when cutter (50) moves to the proximal position, stop member (55) pushes shuttle valve slider (152) proximally such that openings (208) are longitudinally positioned between o-rings (210), thus substantially sealing second lumen (28) until the distal end of sleeve (250) engages the proximal end of shuttle valve slider (152) and begins pushing shuttle valve slider (152) distally to the point where the proximal-most o-ring (210) is moved distal to openings (208). Second lumen (28) is thereby again vented as noted above. Thus, valve mechanism (150) of the present example substantially seals off second lumen (28) relative to atmosphere when cutter (50) is at a proximal position and when cutter (50) is at initial stages of advancement; while venting second lumen (28) to atmosphere when cutter (50) is at other positions.

It should be understood that, as with other components described herein, valve mechanism (150) may be varied, modified, substituted, or supplemented in a variety of ways; and that valve mechanism (150) may have a variety of alternative features, components, configurations, and functionalities. Suitable alternative versions, features, components, configurations, and functionalities of valve mechanism (150) will be apparent to those of ordinary skill in the art in view of the teachings herein.

Exemplary Tissue Sample Holder

As shown in FIGS. 1-4, tissue sample holder (40) of the present example comprises a cap (42), an outer cup (44), and a filter tray (46). Cup (44) is secured to probe (12) in the present example. Such engagement may be provided in any suitable fashion. Outer cup (44) of the present example is substantially transparent, allowing the user to view tissue samples on filter tray (46), though outer cup (44) may have any other suitable properties if desired.

Outer cup (44) is in fluid communication with cutter lumen (52) and with vacuum pump (38) in the present example. In particular, outer cup (44) is in fluid communication with cutter lumen (52) via a first port (45); and is in fluid communication with vacuum pump (38) via a second port (47). A conduit (not shown) couples port (41) of vacuum pump (38) with second port (47) of outer cup (44). In the present example, second port (47) is further coupled with a hydrophobic filter (48), which is in fluid communication with the interior space defined by outer cup (44). In addition to or in lieu of having hydrophobic filter (48) a highly absorbent material may be provided in tissue sample holder (40) to soak up liquids. Alternatively, liquids may be dealt with in any other suitable fashion. In the present example, vacuum pump (38) may thus be used to induce a vacuum in cutter lumen (52); with such a vacuum being communicated through conduit (39), ports (41, 45, 47), and the interior of outer cup (44).

Filter tray (46) of the present example has a basket-like configuration, and has plurality of openings (47) formed therethrough. Openings (47) are sized and configured to permit the passage of fluids therethrough while preventing the passage of tissue samples therethrough. Filter tray (46) is thus configured to receive tissue samples that are communicated proximally through cutter (50) as will be described in greater detail below. It should be understood that filter tray (46) may take a variety of alternate forms.

Cap (42) is removably coupled with outer cup (44) in the present example. An o-ring (53) provides a seal when cap (42) is engaged with outer cup (44). A vacuum may thus be maintained within outer cup (44) when cap (42) is secured to outer cup (44). In operation, a user may remove cap (42) to access tissue samples that have gathered on filter tray (46) during a biopsy process.

Tissue sample holder (40) of the present example is configured to hold at least ten tissue samples. Alternatively, tissue sample holder (40) may be configured to hold any other suitable number of tissue samples. It should be understood that, as with other components described herein, tissue sample holder (40) may be varied, modified, substituted, or supplemented in a variety of ways; and that tissue sample holder (40) may have a variety of alternative features, components, configurations, and functionalities. For instance, tissue sample holder (40) may be alternatively configured such that it has a plurality of discrete tissue sample compartments that may be selectively indexed to cutter lumen (52). Such indexing may be provided automatically or manually. By way of example only, tissue sample holder (40) may be configured and operable in accordance with the teachings of U.S. Pub. No. 2008/0195066, entitled "Revolving Tissue Sample Holder for Biopsy Device," published Aug. 14, 2008, the disclosure of which is incorporated by reference herein; U.S. Non-Provisional patent application Ser. No. 12/337,997, entitled "Tissue Biopsy Device with Rotatably Linked Thumbwheel and Tissue Sample Holder," filed Dec. 18, 2008; U.S. Non-Provisional patent application Ser. No. 12/337,911, entitled "Biopsy Device with Discrete Tissue Chambers," filed Dec. 18, 2008, the disclosure of which is incorporated by reference herein; or U.S. Non-Provisional patent application Ser. No. 12/337,874, entitled "Mechanical Tissue Sample Holder Indexing Device," filed Dec. 18, 2008, the disclosure of which is incorporated by reference herein. Other suitable alternative versions, features, components, configurations, and functionalities of tissue sample holder (40) will be apparent to those of ordinary skill in the art in view of the teachings herein. Alternatively, tissue sample holder (40) may simply be omitted, if desired.

Exemplary Cutter

As shown in FIG. 5, cutter (50) of the present example is substantially hollow, such that cutter (50) defines a cutter lumen (52). Cutter (50) also has a substantially sharp distal edge (51), such that cutter (50) is operable to sever a biopsy sample from tissue protruding through lateral aperture (24) of needle (20). Alternatively, the distal end of cutter (50) may have any other suitable configuration. As shown in FIGS. 3-4, a proximal portion of cutter (50) extends into tissue sample holder (40). A vacuum created in tissue sample holder (40) by vacuum pump (38) is thus communicated to cutter lumen (52). A seal (54) is provided at the interface of cutter (50) and outer cup (44). Seal (54) is configured to substantially seal the interface of cutter (50) and mount (42). Furthermore, cutter (50) is configured such that it remains in sealed fluid communication with the interior of tissue sample holder (40) even when cutter (50) is in a distal most position. Of course, cutter (50) may have any other suitable alternative features or configurations. Similarly, cutter (50) may have any other suitable alternative relationships with tissue sample holder (40).

It should be understood that, as with other components described herein, cutter (50) may be varied, modified, substituted, or supplemented in a variety of ways; and that cutter (50) may have a variety of alternative features, components, configurations, and functionalities. Suitable alternative versions, features, components, configurations, and functionalities of cutter (50) will be apparent to those of ordinary skill in the art in view of the teachings herein.

Exemplary Cutter Actuation Mechanism

As shown in FIGS. 3-7, cutter actuation mechanism (60) of the present example comprises motor (36), shafts (62, 64), and gears (72, 74, 76). It should be understood that activation of motor (36) will rotate gears (82, 84) in the present example. As shown in FIGS. 3 and 6, motor (36), shafts (62, 64, 68, 69), gears (72, 74, 76, 78, 80, 82, 84), and bearings (70) are all contained within holster (14) in the present example. As shown in FIG. 2, gears (82, 84) are partially exposed by an opening formed in a cover plate (18) of holster (14) in the present example.

Cutter actuation mechanism (60) of the present example further comprises a hex nut (100) and a worm nut (120). Hex nut (100) includes a unitary gear (86). Worm nut (120) also includes a unitary gear (88). Gear (86) is configured to mesh with gear (82) when probe (12) and holster (14) are coupled together; while gear (88) is configured to mesh with gear (84) when probe (12) and holster (14) are coupled together. In particular, and as shown in FIG. 2, gears (86, 88) are partially exposed by an opening formed in a cover plate (16) of probe (12) in the present example. Motor (36) is thus operable to rotatingly drive gears (86, 88) in the present example when probe (12) and holster (14) are coupled together. As described in greater detail below, such rotation of gears (86, 88) will cause cutter (50) to rotate and translate in the present example.

A sleeve (250) is unitarily secured to cutter (50). As best seen in FIGS. 6-7, sleeve (250) comprises a hex portion (252), a smooth portion (254), and a flange (256) separating hex portion (252) from smooth portion (254). Hex nut (100) is slidably positioned over hex portion (252) of sleeve (250). The engagement between sleeve (250) and hex nut (100) is such that rotation of hex nut (100) provides corresponding rotation of sleeve (250), yet hex nut (100) may slide longitudinally relative to sleeve (250). It should be understood that sleeve (250) and hex nut (100) may have a variety of other configurations (e.g., complementary key and keyway instead of hex features, etc.) and relationships.

As noted above, gear (86) of hex nut (100) is configured to mesh with gear (82), such that rotation of gear (82) causes rotation of hex nut (100). Such rotation of hex nut (100) will cause corresponding rotation of cutter (50) as noted above. It will therefore be understood that cutter actuation mechanism (60) may cause rotation of cutter (50) in response to activation of motor (36), with rotation of motor (36) being communicated to cutter (50) through shafts (62, 64, 68, 69), gears (72, 74, 76, 78, 80, 82, 84, 86), hex nut (100), and sleeve (250). Of course, any other suitable structures, components, configurations, or techniques may be used to provide rotation of cutter (50).

Cutter actuation mechanism (60) of the present example further comprises a lead screw (122). Lead screw (122) is positioned about hex portion (252) of sleeve (250), and is configured to rotate unitarily therewith. Lead screw (122) defines a hexagonal opening with six flat faces that are configured to complement the flat faces of sleeve (250), such that rotation of cutter (50) and sleeve (250) provides corresponding rotation of lead screw (122). Lead screw (122) is further secured to hex portion (252) of sleeve (250) by a clip (124), and a washer (126) is positioned between clip (124) and lead screw (122). A first coil spring (128) is positioned between the proximal end of lead screw (122) and washer (126). A second coil spring (130) is positioned between the distal end of lead screw (122) and flange (256) of sleeve (250). The spacing between flange (256) and washer (126) permit some freedom of movement for lead screw (122) along a portion of the length of sleeve (250) between flange (256) and washer (126); while springs (128, 130) bias lead screw (122) to be substantially centered between flange (256) and washer (126). It should be understood that any other suitable type of resilient member may be used in addition to or in lieu of coil springs (128, 130).

Lead screw (122) has external threads (132) that are engaged with internal threads (134) of worm nut (120). Accordingly, lead screw (122) translates relative to worm nut (120) when lead screw (122) rotates relative to worm nut (120) when threads (132, 134) are engaged. However, the interior length of worm nut (120) also includes smooth sections (136) that are distal to and proximal to internal threads (134). Thus, lead screw (122) may not translate relative to worm nut (120) when lead screw (122) rotates relative to worm nut (120) when threads (132) are located at smooth sections (136) (e.g., when threads (132, 134) are not engaged). Worm nut (120) is further supported by a bushing (138) in the present example. It should be understood that, due to engagement of lead screw (122) with flange (256) and washer (126), and due to engagement of sleeve (250) with cutter (250), translation of lead screw (122) relative to worm nut (120) in the present example also results in translation of cutter (50) relative to body (30) in the present example. It should also be understood that sleeve (250), lead screw (122), and worm nut (120) may have a variety of other configurations and relationships. Similarly, a variety of other structures or components may be used in addition to or in lieu of sleeve (250) and/or worm nut (120).

As noted above, gears (82, 84) of holster (14) rotate simultaneously when motor (36) is activated. As further noted above, gears (82, 84) mesh with gears (86, 88) of probe (12) when probe (12) is coupled with holster (14), such that activated motor (36) rotates gears (86, 88) simultaneously. Activated motor (36) will thus rotate hex nut (100) and worm nut (120) simultaneously. It should therefore be understood that sleeve (250), cutter (50), lead screw (122), and worm nut (120) will all rotate simultaneously when motor (36) is activated. It is also noted that gears (82, 84) have different pitch diameters. Gears (86, 88) also have different pitch diameters. Accordingly, even with motor (36) rotating at one rotational speed, hex nut (100) and worm nut (120) rotate simultaneously in the same direction at different rotational speeds. Since rotation of lead screw (122) is driven by rotation of hex nut (100), lead screw (122) and worm nut (120) also rotate simultaneously in the same direction at different rotational speeds. Even though lead screw (122) and worm nut (120) rotate simultaneously in the same direction, the difference between rotational speeds of lead screw (122) and worm nut (120) provide a net result of lead screw (122) rotating relative to worm nut (120), and such relative rotation provides translation of cutter (50) as cutter (50) rotates. By way of example only, with motor (36) providing an output speed of approximately 8,000 rpm, the above-described configuration may provide rotation of cutter (50) at a speed of approximately 1,000 rpm and rotation of worm nut (120) at a speed of approximately 850 rpm, resulting in a net rotation of cutter (50) relative to worm nut (120) at approximately 150 rpm. Of course, any other suitable differential may be provided.

In the present example, cutter (50) is retracted proximally when motor (36) is activated to rotate cutter (50) counterclockwise (viewed from tissue sample holder (40) toward needle (20)); while cutter (50) is advanced distally when motor (36) is activated to rotate cutter (50) clockwise (viewed from tissue sample holder (40) toward needle (20)). The direction of motor (36) rotation may thus be reversed to transition between distal and proximal translation of cutter (50). Alternatively, cutter (50) may instead be rotated clockwise during retraction of cutter (50) and counterclockwise during advancement of cutter (50). Furthermore, cutter actuation mechanism (60) may be configured to be self-reversing, such that cutter (50) may be translated distally and proximally without reversing the direction of motor (36) rotation.

Further exemplary details of cutter actuation mechanism (100) are disclosed in U.S. Non-Provisional patent application Ser. No. 12/483,305, entitled "Tetherless Biopsy Device with Reusable Portion," filed Jun. 12, 2009, the disclosure of which is incorporated by reference herein. Of course, any other suitable structures, components, configurations, or techniques may be used to provide translation and/or rotation of cutter (50). It should therefore be understood that, as with other components described herein, cutter actuation mechanism (60) may be varied, modified, substituted, or supplemented in a variety of ways; and that cutter actuation mechanism (60) may have a variety of alternative features, components, configurations, and functionalities. By way of example only, biopsy device (10) may be configured such that cutter (50) does not translate (e.g., such that cutter (50) merely rotates, etc.); or such that cutter (50) does not rotate (e.g., such that cutter (50) merely translates, etc.). Other suitable alternative versions, features, components, configurations, and functionalities of cutter actuation mechanism (60) will be apparent to those of ordinary skill in the art in view of the teachings herein.

Exemplary Pneumatic Operation

As noted above, vacuum pump (38) may start building a vacuum in cutter lumen (52) as soon as motor (36) is activated; and such a vacuum may continue to build or be maintained as cutter (50) starts moving proximally toward the retraced position. At this stage, second lumen (28) is vented to atmosphere. As cutter (50) moves toward retracted position, such that lateral aperture (24) of needle (20) is "partially open" as shown in FIG. 5, a vacuum in cutter lumen (52) may be further communicated through first lumen (26), which may draw tissue into lateral aperture (24). At this stage, second lumen (28) is still vented to atmosphere. In the present example, second lumen (28) is substantially sealed when cutter (50) reaches a longitudinal position that is proximal to the position shown in FIG. 5, and before cutter (50) reaches the fully retracted position.

When cutter (50) reaches the fully retracted position, such that lateral aperture (24) of needle (20) is "open", a vacuum in cutter lumen (52) may continue to be further communicated through first lumen (26), which may continue to draw tissue into lateral aperture (24). Of course, some amount of tissue may naturally prolapse into lateral aperture (24) without the assistance of vacuum, such that vacuum may not even be needed to draw tissue into lateral aperture (24). At this stage, second lumen (28) is substantially sealed relative to atmosphere. In particular, stop member (55) has pushed shuttle valve slider (152) to a proximal position, such that o-rings (210) "straddle" openings (208) and seal against the interior sidewall of sleeve portion (204) to prevent atmospheric air from being communicated from openings (208) to second lumen (28) via hollow interior (206) of sleeve portion (204).

As motor (36) is reversed and cutter (50) is advanced to sever tissue protruding through lateral aperture (24), vacuum pump (38) may continue to induce a vacuum in cutter lumen (52), and second lumen (28) may eventually be vented to atmosphere. However, in the initial stages of advancement of cutter (50) from the proximal-most position to the distal-most position, the "lost motion" between cutter (50) and shuttle valve slider (152) leaves shuttle valve slider (152) in the proximal position (thereby sealing second lumen (28)) until cutter (50) advances far enough for the distal end of sleeve (250) to engage the proximal end of shuttle valve slider (152). After the distal end of sleeve (250) engages the proximal end of shuttle valve slider (152), and after cutter (50) has continued to move distally to a sufficient degree, the distal end of sleeve (250) eventually pushes shuttle valve slider (152) distally, such that the proximal-most o-ring (210) is eventually moved distal to openings (208) (thereby venting second lumen (28)). As cutter (50) again finally reaches the distal-most position, cutter (50) may completely sever the tissue protruding through lateral aperture (24), with second lumen (28) being vented.

With the severed tissue sample residing in cutter lumen (52), with vacuum pump (38) drawing a vacuum at the proximal face of the severed tissue sample, and with the venting being provided at the distal face of the severed tissue sample (via openings (208), second lumen (28), and openings (27)), the pressure differential applied to the severed tissue sample may cause the severed tissue sample to be drawn proximally through cutter lumen (52) and into tissue sample holder (40). The severed tissue sample may thus be deposited on filter tray (46) of tissue sample holder (40).

Further exemplary details of pneumatic operation are disclosed in U.S. Non-Provisional patent application Ser. No. 12/483,305, entitled "Tetherless Biopsy Device with Reusable Portion," filed Jun. 12, 2009, the disclosure of which is incorporated by reference herein. Of course, any other suitable structures, components, configurations, or techniques may be used to provide selective sealing and/or venting of second lumen (28). Furthermore, in some variations of biopsy device (10), a vacuum, saline, pressurized air, atmospheric air, and/or any other medium may be communicated to second lumen (28) at any suitable stage of operation of biopsy device (10) (e.g., applying vacuum or venting to second lumen (28) during and/or upon retraction of cutter (50) and/or during advancement of cutter (50), sealing second lumen during advancement of cutter (50), etc.). Other suitable alternative structures, components, configurations, or techniques for communicating severed tissue samples proximally through cutter lumen (52) to reach tissue sample holder (40) will be apparent to those of ordinary skill in the art in view of the teachings herein.

Button Activation

Figure 8:
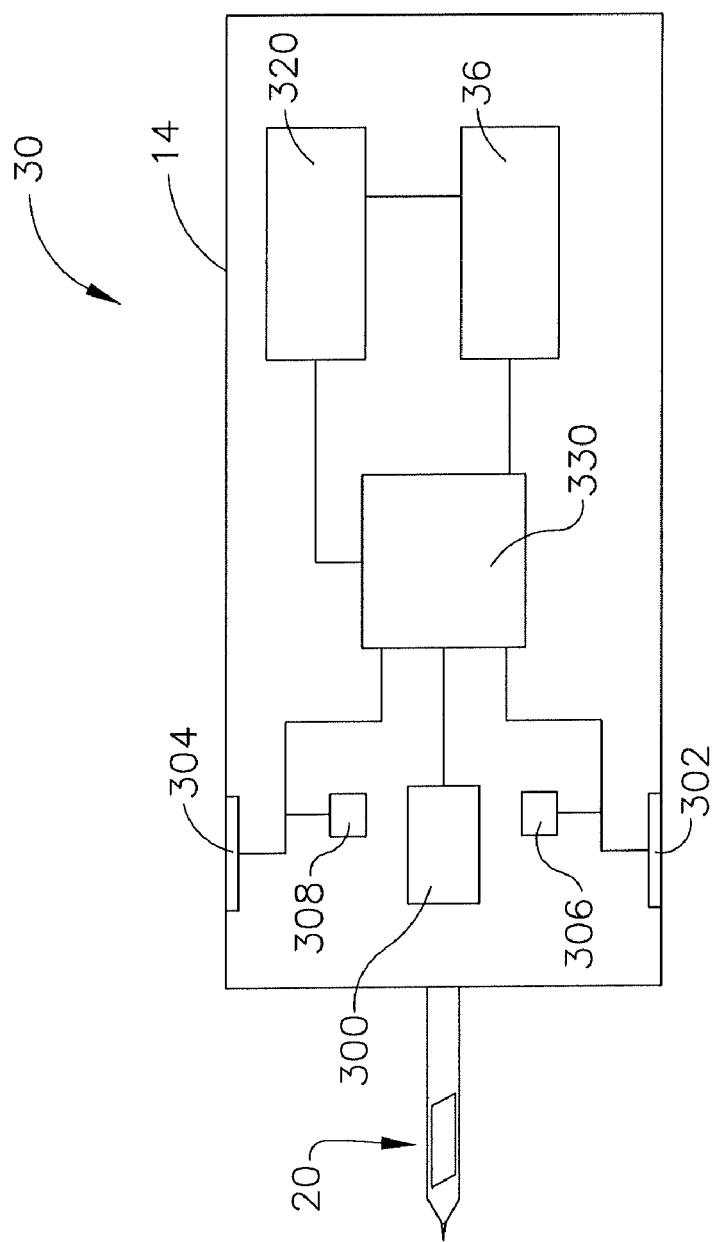
FIG. 8 depicts a schematic view of the biopsy device of FIG. 1, showing exemplary control components.

As shown in FIGS. 1 and 8, biopsy device (10) has a plurality of buttons (300, 302, 304), which may be used to control operation of biopsy device (10). For instance, either of buttons (302, 304) may be used as trigger buttons. That is, an operator may actuate a selected one of trigger buttons (302, 304) to initiate a cutting stroke (e.g., by activating motor (36), etc.). Trigger button (302) may thus provide the same functionality as trigger button (304). As described in greater detail below, biopsy device (10) may be configured such that either trigger button (302, 304) may be used to initiate a cutting stroke; or such that one particular trigger button (302, 304) must be selected to initiate a cutting stroke while the non-selected trigger button (302, 304) is left disabled. It should be noted that the term "trigger button" is intended to encompass a variety of types of structures and devices, and is not limited to just a standard electromechanical button. By way of example only, trigger buttons (302, 304) may include pneumatic buttons, capacitive buttons, inductive buttons, etc. Still other suitable components that may be used to initiate a cutting stroke will be apparent to those of ordinary skill in the art in view of the teachings herein.

As shown in FIG. 8, trigger buttons (302, 304) are in communication with control module (330), which is in communication with battery (320) and motor (36). Battery (320) is also in communication with motor (36). Control module (330) is configured to selectively complete a circuit between battery (320) and motor (36), such that motor (36) may be selectively powered in accordance with an operator's input via trigger buttons (302, 304). Control module (330) may also include a control logic such that control module (330) is operable to selectively reverse the direction of rotation of motor (36) (e.g., to transition between proximal and distal movement of cutter (50), etc.). As used herein, the term "control module" should not be read as necessarily requiring all of the components of control module (330) to be integrated into a single self-contained unit. Indeed, control module (330) may in fact comprise several components that are positioned at various locations within biopsy device (10), with such separate components being in communication with each other to some degree. Suitable components of a control module (330) may include one or more processors and associated circuitry, etc., as will be apparent to those of ordinary skill in the art in view of the teachings herein.

In some versions, the operator need only tap one of trigger buttons (302, 304), or hold one of trigger buttons (302, 304) down for a predetermined period of time, in order to initiate and complete a cutting stroke. In some other versions, the operator needs to hold down one of trigger buttons (302, 304) during the entire cutting stroke. In some such versions, where the selected trigger button (302, 304) is released in the middle of a cutting stroke, the cutting stroke may be paused until the selected trigger button (302, 304) is again actuated.

As shown in FIGS. 1 and 8, one trigger button (302) is on the left-hand side of body (30); while the other trigger button (304) is on the other side of body (30). Those of ordinary skill in the art will understand that any given operator of biopsy device (10) may prefer one trigger button (302) over the other trigger button (304) due to the location of trigger buttons (302, 304). By way of example only, such preference may be dictated at least in part by whether the operator is right-handed or left-handed, the way in which the operator prefers to grip biopsy device (10), etc. Having two trigger buttons (302, 304) will thus allow the operator to select one particular trigger button (302, 304) for operation of biopsy device (10) in accordance with the operator's preference. In some versions, trigger buttons (302, 304) and control module (330) are configured such that the operator may use either or both trigger buttons (302, 304) at any time during a biopsy procedure. In other words, both trigger buttons (302, 304) may be considered "active," and therefore immediately operable/enabled, at all times. The operator may thus switch from using one trigger button (302, 304) to the other trigger button (302, 304), without having to do anything additional in order to switch from using one trigger button (302, 304) to the other trigger button (302, 304).

In some other versions, however, trigger buttons (302, 304) and control module (330) may be configured such that only one trigger button (302, 304) can be enabled at a given time. For instance, trigger buttons (302, 304) and control module (330) may be configured such that a user must select one particular trigger button (302, 304) for activation/enablement; and once such a selection has been made, the other trigger button (302, 304) will be deactivated/disabled for the rest of the biopsy procedure. Such deactivation/disablement may prevent inadvertent activation of biopsy device (10) by inadvertent actuation of the non-selected trigger button (302, 304).

It should be understood that there are a variety of ways in which one particular trigger button (302, 304) may be activated/enabled while the other trigger button (302, 304) is deactivated/disabled. For instance, activation/enablement of a particular trigger button (302, 304) and deactivation/disablement of the other trigger button (302, 304) may be provided electronically. By way of example only, activation/enablement of a particular trigger button (302, 304) may be provided as soon as the operator first actuates the particular trigger button (302, 304). In some such versions, control module (330) may include a logic that is configured to sense which particular trigger button (302, 304) was first actuated, and that may designate that particular trigger button (302, 304) as the activated/enabled trigger button (302, 304). Such a logic in control module (330) may also designate or treat the other trigger button (302, 304) as the deactivated/disabled trigger button (302, 304). In other words, as soon as a first trigger button (302, 304) is actuated, control module (330) may permit biopsy device (10) to be controlled by that first trigger button (302, 304) while preventing biopsy device (10) from being controlled by the other trigger button (302, 304).

As another merely illustrative example, electronic activation/enablement and deactivation/disablement may be provided by logic in control module (330) in response to the operator actuating a selected trigger button (302, 304) in a particular way. For instance, control module (330) may be programmed with logic to sense when a particular trigger button (302, 304) is "double clicked." That is, biopsy device (10) may be configured such that the operator may activate/enable a selected trigger button (302, 304) by "double clicking" it. Once the first trigger button (302, 304) has been double clicked, logic in control module (330) may designate or treat the other trigger button (302, 304) as the deactivated/disabled trigger button (302, 304), such that biopsy device (10) cannot be controlled by the deactivated/disabled trigger button (302, 304). Alternatively, control module (330) may be programmed with logic to sense when a particular trigger button (302, 304) has been actuated in some other predetermined pattern or number of times (e.g., three times within a certain period of time, once for a duration of three seconds, etc.); and may designate the active/enabled trigger button (302, 304) in response to such operator input.

As yet another merely illustrative example, electronic activation/enablement and deactivation/disablement may be provided in response to the operator actuating a selection button or switch. For instance, in the present example, button (300) may be used to turn on biopsy device (10) and to select which trigger button (302, 304) to activate/enable. In some such versions, button (300) is operable to turn biopsy device (10) on or off when button (300) is actuated for a certain period of time (e.g., three seconds, etc.). The required actuation duration may differ for turning biopsy device (10) on versus turning biopsy device (10) off. For instance, biopsy device (10) may be turned on when button (300) is merely tapped; while button (300) must be held down for at least three seconds in order to turn biopsy device (10) off. Once biopsy device (10) is turned on, the operator may tap button (300) to select a particular trigger button (302, 304) for activation/enablement.

In some versions where button (300) may be used to select a particular trigger button (302, 304) for activation/enablement, each trigger button (302, 304) may have an associated LED (306, 308) indicating whether the trigger button (302, 304) is activated/enabled; and tapping button (300) may toggle between trigger buttons (302, 304) and their associated LED (306, 308). In other words, button (300) may be used to program control module (300) to select which trigger button (302, 304) is to be activated/enabled and which trigger button (302, 304) is to be deactivated/disabled; and control module (300) may also a logic configured to illuminate the LED (306, 308) that is associated with the activated/enabled trigger button (302, 304) to provide visual feedback to the operator. To the extent that such LEDs (306, 308) are used, such LEDs may be positioned at any suitable location, including but not limited to in or on body (30) next to their associated trigger button (302, 304). In addition or in the alternative, the activated/enabled trigger button (302, 304) may itself be illuminated.

In some versions where visual feedback is provided to indicate which particular trigger button (302, 304) is activated/enabled (e.g., through LEDs (306, 308) and/or through illumination of activated/enabled trigger button (302, 304), etc.), visual feedback may also be provided to indicate that a trigger button (302, 304) needs to be selected for activation. For instance, as soon as biopsy device (10) is turned on, LEDs (306, 308) or trigger buttons (302, 304) may both flash, indicating to the operator that the operator must select one particular trigger button (302, 304) for activation/enablement. As soon as the operator selects a preferred trigger button (302, 304) for activation/enablement, the LEDs (306, 308) or trigger buttons (302, 304) may stop flashing, the selected LED (306, 308) or trigger button (302, 304) may illuminate, and the non-selected LED (306, 308) or trigger button (302, 304) may go dark. Of course, a variety of other types of visual indication may be provided to indicate which trigger button (302, 304) has been selected for activation/enablement. Other suitable ways in which such visual indication may be provided will be apparent to those of ordinary skill in the art in view of the teachings herein. Similarly, other suitable ways in which electronic activation/enablement and deactivation/disablement of trigger buttons (302, 304) may be provided will be apparent to those of ordinary skill in the art in view of the teachings herein.

In versions where electronic activation/enablement and deactivation/disablement of trigger buttons (302, 304) is provided, an operator's selection of a preferred trigger button (302, 304) may be stored in a non-volatile memory within body (30). In other words, if the operator turns off biopsy device (10) and later turns biopsy device (10) back on, such memory may recall the operator's preference of trigger button (302, 304), such that the operator does not need to re-designate the preferred trigger button (302, 304). Alternatively, an operator's selection of a preferred trigger button (302, 304) may be stored in a volatile memory within body (30), such that an operator must re-designate the preferred trigger button (302, 304) after biopsy device (10) is turned off and then turned back on. As yet another merely illustrative variation, control module (330) may be configured such that the operator must designate the preferred trigger button (302, 304) before each cutting stroke is initiated, even if biopsy device (10) has not been turned off/on between cutting strokes.

Figure 9:
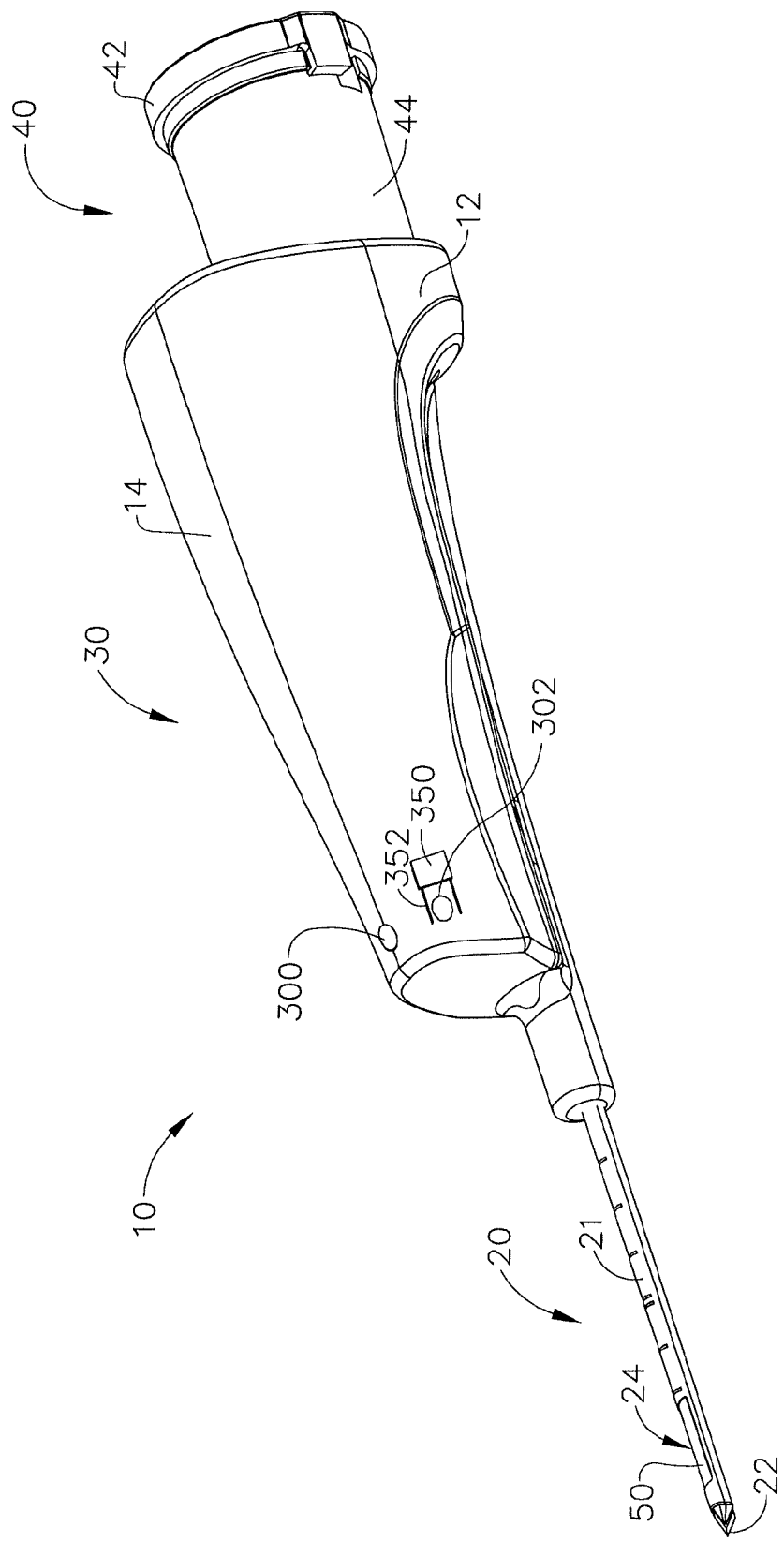
FIG. 9 depicts a perspective view of an exemplary alternative biopsy device.

Still another merely illustrative example is illustrated in FIG. 9, in which activation/enablement of a particular trigger button (302, 304) and deactivation/disablement of the other trigger button (302, 304) may be provided mechanically. In particular, FIG. 9 shows a sliding cover (350), which is positioned adjacent to trigger button (302), and which is slidable along rails (352). Rails (352) are integral with body (300) in the present example. It should be understood that trigger button (304) may also have a sliding cover (350). Cover (350) is shown in FIG. 9 as leaving trigger button (302) exposed, thereby permitting trigger button (302) to be actuated. In this example, a cover (350) may be slid over trigger button (304), such that actuation of trigger button (302) is permitted while actuation of trigger button (304) is prevented. The operator may thus select which trigger button (302, 304) should be enabled and which trigger button (302, 304) should be disabled simply by sliding covers (350) to selectively expose or cover trigger buttons (302, 304) in accordance with the operator's preference. While sliding covers (350) are shown as providing selective exposure/covering of trigger buttons (302, 304), it should be understood that a variety of other structures may be used to provide selective exposure/covering of trigger buttons (302, 304) (e.g., pivoting cover, swinging cover, snap-on cover, etc.). Still other suitable ways in which trigger buttons (302, 304) may be mechanically selectively covered or exposed will be apparent to those of ordinary skill in the art in view of the teachings herein.

While button (300) is described above as being usable to turn biopsy device (10) on and off, and/or to provide selection of which trigger button (302, 304) is to be activated, it should be understood that button (300) may be used as yet another trigger button (300, 302, 304). For instance, button (300) may be provided as another available trigger button, just like trigger buttons (302, 304), in addition to or as an alternative to button (300) having the other functionality described above. Button (300) may thus be selected by an operator who prefers the location of button (300) at the top of body (30) over the location of trigger buttons (302, 304) on the sides of body (30). In such versions, when button (300) is selected as the preferred trigger button, actuation of button (300) may initiate a cutting stroke, etc. Similarly, while two trigger buttons (302, 304) and three trigger buttons (300, 302, 304) are discussed above, it should be understood that any suitable number of trigger buttons (302, 304) may be provided and available for selection. Such additional trigger buttons (302, 304) may be provided in any suitable location—on body (30) (e.g., on probe (12) or holster (14)), remotely via an electrical cable (e.g., using footswitch and/or using a vacuum control module, etc.), remotely via an wireless activation (e.g., using footswitch and/or using a vacuum control module, etc.), or elsewhere.

In some versions, some other switch is used to select a particular trigger button (302, 304) for activation/enablement. For instance, biopsy device (10) may include a slider switch or toggle switch to provide selection of which trigger button (302, 304) is to be activated/enabled. As described above, control module (330) may include a logic that is configured to deactivate/disable whichever trigger button (302, 304) is not selected, such that biopsy device (10) will simply not respond to actuation of the non-selected trigger button (302, 304). Still other ways in which selection of a trigger button (302, 304)—electronic, mechanical, both, or otherwise—may be provided will be apparent to those of ordinary skill in the art in view of the teachings herein.

It should also be understood that the concepts of selectively enabled buttons (302, 304) described herein may be applied to a variety of other devices. By way of example only, the concepts of selectively enabled buttons (302, 304) described herein may be applied to any biopsy device that is disclosed in any patent, patent publication, or patent application that is cited herein. Various ways in which the concepts of selectively enabled buttons (302, 304) described herein may be applied to such biopsy devices will be apparent to those of ordinary skill in the art in view of the teachings herein. Furthermore, the concepts of selectively enabled buttons (302, 304) described herein may be applied to virtually any type of device—whether a biopsy device or some other type of device. It is therefore contemplated that the concepts of selectively enabled buttons (302, 304) described herein are certainly not limited to the particular biopsy device (10) described herein.

Exemplary Method of Operation

In a merely exemplary use of biopsy device (10), a user first inserts tissue piercing tip (22) into the breast of a patient. During such insertion, cutter (50) may be advanced to the distal-most position, such that lateral aperture (24) of needle (20) is closed. As also noted herein, such insertion may be performed under visual guidance, stereotactic guidance, ultrasound guidance, MRI guidance, PEM guidance, BSGI guidance, palpatory guidance, some other type of guidance, or otherwise. With needle (20) sufficiently inserted into the patient's breast, the user may select which particular trigger button (302, 304) to use, such as by double-clicking on the selected trigger button (302, 304), sliding a cover (350) to reveal the selected trigger button (302, 304), etc. The user may then activate motor (36), which may in turn activate vacuum pump (38) and cutter actuation mechanism (100), by actuating the selected trigger button (302, 304). Such activation of vacuum pump (38) may induce a vacuum in tissue sample holder (40) and cutter lumen (52) as described above. Such activation of cutter actuation mechanism (60) may cause cutter (50) to rotate counterclockwise and translate proximally, as shown in FIGS. 5-7. As cutter (50) starts retracting, and when cutter (50) reaches the retracted position, vacuum from vacuum pump (38) (as communicated through tissue sample holder (40) and cutter lumen (52)) may draw tissue into lateral aperture (24) of needle (20). During this time, second lumen (28) may be vented by valve mechanism (150).

Once cutter (50) reaches a proximal-most position, vacuum may still be communicated through vacuum lumen (52) and first lumen (26), drawing tissue into lateral aperture (24) of needle (20). Second lumen (28) is substantially sealed by valve assembly (150) at this time. In addition, lead screw (122) freewheels yet is biased distally by spring (128) as cutter (50) continues to rotate counterclockwise. Lateral aperture (24) is fully open at this stage, with tissue prolapsed therein.

The rotation direction of motor (36) is then reversed and cutter (50) begins to advance distally until again reaching the distal-most position. As cutter (50) advances distally, vacuum is still being communicated through vacuum lumen (52), helping to hold tissue in place as sharp distal edge (51) of cutter (50) begins to sever the tissue. Second lumen (28) is initially substantially sealed by valve assembly (150) at this time, but is eventually vented. Cutter (50) then reaches the distal-most position, thereby "closing" lateral aperture (24), and such that sharp distal edge (51) of cutter (50) completely severs the tissue. Vacuum is still being communicated through cutter lumen (52) at this time, and valve assembly (150) vents second lumen (28). As described above, this combination of vacuum and venting provides communication of the severed tissue sample proximally through cutter lumen (52) and into tissue sample holder (40). Motor (36) may continue to operate at the end of the cutting stroke, thereby continuing to drive vacuum pump (38) to maintain a vacuum in tissue sample holder (40). In addition, spring (130) biases lead screw (122) proximally to engage threads (132), while allowing cutter (50) to continue rotating at the distal-most position. A cutting stroke will thus be complete, and may be initiated as many times as desired to acquire additional tissue samples.

As noted above, several cutting strokes may be performed to acquire several tissue samples without the user having to withdraw needle (20) from the patient's breast. The user may adjust the orientation of lateral aperture (24) about the axis defined by needle (20) by rotating the entire biopsy device (10) between cutting strokes for multiple sample acquisition. Alternatively, biopsy device (10) may be configured such that needle (20) is rotatable relative to body (30), such that needle (20) may be rotated via a thumbwheel or other feature. Once the desired number of tissue samples have been obtained, the user may withdraw needle (20) from the patient's breast. The user may then remove cap (42) from cup (44) and retrieve the tissue samples from filter tray (46).

At the end of a procedure, the user may separate probe (12) from holster (14). Holster (14) may then be cleaned and/or sterilized for subsequent use. Probe (12) may be disposed of. Alternatively, as noted above, biopsy device (10) may alternatively be formed as a unitary construction, such that there is no probe (12) separable from a holster (14).

It should be understood that any of a variety of operations may occur at the end of a cutting stroke. For instance, biopsy device (10) may provide a variety of forms of feedback to inform the user that a cutting stroke as been completed. By way of example only, biopsy device (10) may provide an electronic beep or other audible indication, a mechanical audible indication (e.g., a loud click), a visual indication (e.g., a light illuminating or flashing), or some other type of audible and/or visual indication. Alternatively, and particularly in versions where cup (44) is transparent, the user may know that a cutting stroke is complete by simply watching tissue sample holder (40) until the user sees a tissue sample being deposited on filter tray (46). Alternatively, control module (330) may automatically deactivate motor (36) as soon as a cutting stroke is complete, even if the user continues to hold a trigger button (302, 304) down. The user may then initiate another cutting stroke by releasing and then re-pressing the trigger button (302, 304). As yet another merely illustrative example, control module (330) may initiate a cutting stroke in response to the user briefly pressing or tapping a trigger button (302, 304), and may automatically deactivate motor (36) as soon as the cutting stroke is complete. The user may then initiate another cutting stroke by briefly pressing or tapping the trigger button (302, 304) again. Still other suitable ways in which biopsy device (10) may operate at the end of a cutting stroke and/or to initiate a subsequent cutting stroke will be apparent to those of ordinary skill in the art in view of the teachings herein.

It should also be understood that control module (330) may include circuitry that is configured to automatically cause the rotational direction of motor (36) to reverse as soon as cutter (50) reaches the proximal-most position. For instance, one or more sensors (e.g., hall effect sensor, etc.) may track or otherwise sense the longitudinal position of cutter (50). In addition or in the alternative, one or more sensors (e.g., encoder with encoder wheel, etc.) may track or otherwise sense the number of rotations of cutter (50), and control module (330) may understand the longitudinal position of cutter (50) as a function of the number of rotations of cutter (50). As yet another alternative, motor reversal may be essentially manual (e.g., such that biopsy device (10) includes a "forward" button and a "reverse" button, etc.). Still other suitable ways in which the rotational direction of motor (38) may be manually or automatically reversed will be apparent to those of ordinary skill in the art in view of the teachings herein. It should also be understood that control module (330) may continue to operate motor (36) at least temporarily (e.g., for a few seconds, etc.) at the end of each cutter (50) stroke (e.g., while cutter (50) remains at the distal-most position and/or at the proximal-most position), such as to continue to operate vacuum pump (38).

In versions of biopsy device (10) where an electronic based audible and/or visual indication of the end of a cutting stroke is provided, as well as versions of biopsy device (10) where control module (330) automatically deactivates motor (36) or disengages a clutch or provides some other type of automated response, there are a variety of ways in which the end of a cutting stroke may be sensed. For instance, a portion of cutter (50) may include a magnet, and a hall effect sensor may be positioned in body (30) to sense the presence of the magnet when cutter (50) reaches the distal-most position at the end of a cutting stroke. As another merely illustrative example, an encoder wheel may be coupled with cutter (50) or a rotating component of cutter rotation mechanism (60), such that the longitudinal position of cutter (50) may be determined based on a number of rotations. Other suitable ways in which the end of a cutting stroke may be sensed (e.g., electronically, mechanically, electro-mechanically, manually, etc.) will be apparent to those of ordinary skill in the art in view of the teachings herein.

Of course, the above examples of use of biopsy device (10) are merely illustrative. Other suitable ways in which biopsy device (10) may be used will be apparent to those of ordinary skill in the art in view of the teachings herein. It should also be understood that at least a portion of biopsy device (10) may be configured and/or usable in accordance with the teachings of U.S. Non-Provisional patent application Ser. No. 12/483,305, entitled "Tetherless Biopsy Device with Reusable Portion," filed Jun. 12, 2009, the disclosure of which is incorporated by reference herein. As additional merely illustrative alternatives, at least a portion of biopsy device (10) may be configured and/or usable in accordance with the teachings of any patent, patent publication, or patent application that is cited herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy device, comprising:
   (a) a needle having a transverse aperture;
   (b) a cutter, wherein the cutter is movable relative to the needle to sever tissue protruding into the transverse aperture;
   (c) a body, wherein the needle extends distally from the body, wherein the body comprises:
      (i) a cutter actuation mechanism, wherein the cutter actuation mechanism is operable to move the cutter relative to the needle to sever tissue protruding into the transverse aperture,
      (ii) at least two trigger buttons, and
      (iii) a control module in communication with the cutter actuation mechanism and the at least two trigger buttons, wherein the control module includes a button selection logic configured to receive a user's button selection input, wherein the user's button selection logic is selected via at least one of the at least two trigger buttons, the button selection logic is further configured to enable one selected trigger button of the at least two trigger buttons and disable the non-selected trigger button of the at least two trigger buttons in accordance with the user's button selection input, wherein the enabled trigger button is operable to activate the cutter actuation mechanism, wherein the disabled trigger button is not operable to activate the cutter actuation mechanism.

2. The biopsy device of claim 1, wherein the button selection logic is configured to receive the user's button selection input as being represented by whichever trigger button of the at least two trigger buttons the user actuates first.

3. The biopsy device of claim 1, wherein the button selection logic is configured to receive the user's button selection input as being represented by whichever trigger button of the at least two trigger buttons the user double clicks.

4. The biopsy device of claim 1, wherein the button selection logic is configured to recognize the user's button selection input as being represented by whichever trigger button of the at least two trigger buttons the user holds down for a predetermined period of time.

5. The biopsy device of claim 1, wherein the body further comprises a button selector, wherein the button selector is in communication with the button selection logic of the control module, wherein the button selector is operable to receive and transmit the user's button selection input to the button selection logic.

6. The biopsy device of claim 4, wherein the button selector comprises a button that is separate from the at least two trigger buttons.

7. The biopsy device of claim 1, wherein the body further comprises at least one visual indicator in communication with the control module, wherein the visual indicator is configured to visually indicate which trigger button of the at least two trigger buttons has been selected for enablement.

8. The biopsy device of claim 7, wherein the at least one visual indicator comprises a plurality of LEDs, wherein each LED of the plurality of LEDs is associated with a corresponding trigger button of the at least two trigger buttons.

9. The biopsy device of claim 1, wherein the body comprises a left side and a right side, wherein a first trigger button of the at least two trigger buttons is positioned on the left side of the body, wherein a second trigger button of the at least two trigger buttons is positioned on the right side of the body.

10. The biopsy device of claim 9, wherein a third trigger button of the at least two trigger buttons is positioned between the first and second trigger buttons.

11. The biopsy device of claim 1, wherein the control module is configured to activate the cutter actuation mechanism in response to a user tapping on the enabled trigger button.

12. The biopsy device of claim 1, wherein the cutter actuation mechanism comprises a motor.

13. The biopsy device of claim 12, wherein the motor is positioned within the body.

14. The biopsy device of claim 1, further comprising a battery in communication with the control module, wherein the battery is configured to provide power to the cutter actuation mechanism.

15. The biopsy device of claim 14, wherein the battery is positioned within the body.

16. The biopsy device of claim 1, wherein the cutter actuation mechanism is operable to rotate the cutter relative to the needle.

17. The biopsy device of claim 16, wherein the cutter actuation mechanism is operable to translate the cutter relative to the needle.

18. A biopsy device, comprising:
   (a) a needle having a transverse aperture;
   (b) a cutter, wherein the cutter is movable relative to the needle to sever tissue protruding into the transverse aperture;
   (c) a body, wherein the needle extends distally from the body, wherein the body comprises:
      (i) a cutter actuation mechanism, wherein the cutter actuation mechanism is operable to move the cutter relative to the needle to sever tissue protruding into the transverse aperture,
      (ii) at least two trigger buttons, wherein each of the at least two trigger buttons are capable of performing substantially the same functionality, and
      (iii) a control module in communication with the cutter actuation mechanism and the at least two trigger buttons,
      wherein the biopsy device is configured such that the at least two trigger buttons are selectively enabled and disabled, such that a selectively enabled trigger button of the at least two trigger buttons is operable to activate the cutter actuation mechanism, and such that a selectively disabled trigger button of the at least two trigger buttons is not operable to activate the cutter activation mechanism.

19. The biopsy device of claim 18, wherein the body further comprises a plurality of button covers, wherein each button cover is associated with a corresponding trigger button of the at least two trigger buttons, wherein each button cover is operable to selectively cover or expose its corresponding trigger button, such that a covered trigger button of the at least two trigger buttons is disabled while an exposed trigger button of the at least two trigger buttons is enabled.

* * * * *